(12) United States Patent
Strasfeld et al.

(10) Patent No.: US 11,793,594 B2
(45) Date of Patent: Oct. 24, 2023

(54) SYSTEM AND METHOD FOR THRESHOLDING FOR RESIDUAL CANCER CELL DETECTION

(71) Applicant: Lumicell, Inc., Newton, MA (US)

(72) Inventors: David B. Strasfeld, Somerville, MA (US); Jorge Ferrer, Isabela, PR (US); W. David Lee, Brookline, MA (US)

(73) Assignee: Lumicell, Inc., Newton, MA (US)

( * ) Notice: Subject to any disclaimer, the term of this patent is extended or adjusted under 35 U.S.C. 154(b) by 805 days.

(21) Appl. No.: 16/708,486

(22) Filed: Dec. 10, 2019

(65) Prior Publication Data

US 2020/0205930 A1 Jul. 2, 2020

Related U.S. Application Data

(60) Provisional application No. 62/786,657, filed on Dec. 31, 2018.

(51) Int. Cl.
| | | |
|---|---|---|
| *G06T 7/00* | (2017.01) | |
| *A61B 5/00* | (2006.01) | |
| *A61B 90/00* | (2016.01) | |
| *G01N 21/31* | (2006.01) | |
| *G01N 21/64* | (2006.01) | |

(52) U.S. Cl.
CPC .......... *A61B 90/361* (2016.02); *A61B 5/0036* (2018.08); *A61B 5/0071* (2013.01); *A61B 5/0082* (2013.01); *A61B 90/37* (2016.02); *G01N 21/31* (2013.01); *G01N 21/6428* (2013.01); *G01N 21/6447* (2013.01); *G06T 7/0012* (2013.01); *A61B 2090/3612* (2016.02); *G01N 2021/6495* (2013.01); *G06T 2207/30096* (2013.01)

(58) Field of Classification Search
None
See application file for complete search history.

(56) References Cited

U.S. PATENT DOCUMENTS

| | | |
|---|---|---|
| 10,791,937 B2 | 10/2020 | Lee et al. |
| 10,813,554 B2 | 10/2020 | Lee et al. |
| 11,426,075 B1 | 8/2022 | Strasfield et al. |
| | (Continued) | |

FOREIGN PATENT DOCUMENTS

| | | |
|---|---|---|
| JP | 2007/233036 A | 9/2007 |
| WO | WO 95/14979 A1 | 6/1995 |

OTHER PUBLICATIONS

U.S. Appl. No. 14/847,434, filed Sep. 8, 2015, Lee et al.
(Continued)

*Primary Examiner* — Samah A Beg
(74) *Attorney, Agent, or Firm* — Wolf, Greenfield & Sacks, P.C.

(57) ABSTRACT

Embodiments related to methods of use of an image analysis system for identifying residual cancer cells after surgery are disclosed. In some embodiments, a patient-specific threshold used to detect abnormal cells in a surgical site can be determined. A medical imaging device can be configured to produce a set of images of an anatomy of a patient. An image analysis system, comprising one or more processors, can be configured to receive the set of images, and analyze the set of images to determine a patient-specific threshold to use to detect abnormal tissue of the patient.

24 Claims, 6 Drawing Sheets

(56) References Cited

U.S. PATENT DOCUMENTS

| | | | |
|---|---|---|---|
| 11,446,088 | B2 | 8/2022 | Lee et al. |
| 11,471,056 | B2 | 9/2022 | Lee et al. |
| 2006/0173162 | A1 | 8/2006 | Djurup et al. |
| 2006/0173560 | A1 | 8/2006 | Widrow |
| 2009/0299196 | A1 | 12/2009 | Bawendi et al. |
| 2010/0158332 | A1 | 6/2010 | Rico et al. |
| 2011/0021908 | A1 | 1/2011 | Lee et al. |
| 2011/0104071 | A1 | 5/2011 | Lee et al. |
| 2011/0245657 | A1 | 10/2011 | Degani et al. |
| 2012/0150164 | A1 | 6/2012 | Lee et al. |
| 2014/0016845 | A1* | 1/2014 | Gazit .................. G06T 7/38 382/130 |
| 2014/0276102 | A1 | 9/2014 | Lee et al. |
| 2014/0276103 | A1 | 9/2014 | Lee et al. |
| 2016/0025632 | A1* | 1/2016 | Lee .................. G01N 33/4833 506/10 |
| 2020/0225160 | A1 | 7/2020 | Lee et al. |
| 2022/0387108 | A1 | 12/2022 | Lee et al. |

OTHER PUBLICATIONS

U.S. Appl. No. 15/721,247, filed Sep. 29, 2017, Lee et al.
U.S. Appl. No. 16/368,073, filed Mar. 28, 2019, Lee et al.
U.S. Appl. No. 14/211,201, filed Mar. 14, 2014, Lee et al.
U.S. Appl. No. 15/206,754, filed Jul. 11, 2016, Lee et al.
U.S. Appl. No. 14/211,259, filed Mar. 14, 2014, Lee et al.
U.S. Appl. No. 15/684,627, filed Aug. 23, 2017, Strasfeld et al.
PCT/US2019/065319, Feb. 24, 2020, International Search Report and Written Opinion.
U.S. Appl. No. 16/829,498, filed Mar. 25, 2020, Lee et al.
International Search Report and Written Opinion for International Application No. PCT/US2019/065319, dated Feb. 24, 2020.
[No Author Listed], Cathepsin Activatable Fluorescent Probe. Clinical Trials. Jun. 21, 2012. (https://clinicaltrials.gov/archive/NCT01626066/2012_06_21) [last accessed May 27, 2015].
Anikijenko et al., In vivo detection of small subsurface melanomas in athymic mice using noninvasive fiber optic confocal imaging. J Invest Dermatol. Dec. 2001;117(6):1442-8.
Bach et al., Elevated lysosomal pH in Mucolipidosis type IV cells. Clin Chim Acta. Feb. 1999;280(1-2):173-9.
Bates et al., Short-range spectroscopic ruler based on a single-molecule optical switch. Phys Rev Lett. Mar. 18, 2005;94(10):108101. Epub Mar. 15, 2005.
Bigio et al., Diagnosis of breast cancer using elastic-scattering spectroscopy: preliminary clinical results. J Biomed Opt. Apr. 2000;5(2):221-8.
Blum et al., Noninvasive optical imaging of cysteine protease activity using fluorescently quenched activity-based probes. Nat Chem Biol. Oct. 2007;3(10):668-77. Epub Sep. 9, 2007.
Brigman, Preliminary Analysis of Phase 1, First-In-Human, Cathepsin Activated Tumor Imaging Probe. Presentation. Nov. 2013. 29 pages.
Cheng et al., Near-infrared fluorescent RGD peptides for optical imaging of integrin alphavbeta3 expression in living mice. Bioconjug Chem. Nov.-Dec. 2005;16(6):1433-41.
Cuneo et al., Imaging primary mouse sarcomas after radiation therapy using cathepsin-activatable fluorescent imaging agents. Int J Radiat Oncol Biol Phys. May 1, 2013;86(1):136-42. doi: 10.1016/j.ijrobp.2012.12.007. Epub Feb. 4, 2013.

Dacosta et al., New optical technologies for earlier endoscopic diagnosis of premalignant gastrointestinal lesions. J Gastroenterol Hepatol. Feb. 2002;17 Suppl:S85-104.
De Grand et al., Tissue-like phantoms for near-infrared fluorescence imaging system assessment and the training of surgeons. J Biomed Opt. Jan.-Feb. 2006;11(1):014007.
Demos et al., Near-infrared autofluorescence imaging for detection of cancer. J Biomed Opt. May-Jun. 2004;9(3):587-92.
Funovics et al., Protease sensors for bioimaging. Anal Bioanal Chem. Nov. 2003;377(6):956-63. Epub Sep. 3, 2003.
Gleysteen et al., Fluorescent labeled anti-EGFR antibody for identification of regional and distant metastasis in a preclinical xenograft model. Head Neck. Jun. 2008;30(6):782-9. doi: 10.1002/hed.20782.
Graves et al., A submillimeter resolution fluorescence molecular imaging system for small animal imaging. Med Phys. May 2003;30(5):901-11.
Gray et al., Dual-mode laparoscopic fluorescence image-guided surgery using a single camera. Biomed Opt Express. Aug. 1, 2012;3(8):1880-90. doi: 10.1364/BOE.3.001880. Epub Jul. 17, 2012.
Hart et al., Cell binding and internalization by filamentous phage displaying a cyclic Arg-Gly-Asp-containing peptide. J Biol Chem. Apr. 29, 1994;269(17):12468-74.
Hingtgen et al., Real-time multi-modality imaging of glioblastoma tumor resection and recurrence. J Neurooncol. Jan. 2013;111(2):153-61. doi: 10.1007/s11060-012-1008-z. Epub Dec. 16, 2012.
Hsiung et al., Detection of colonic dysplasia in vivo using a targeted heptapeptide and confocal microendoscopy. Nat Med. Apr. 2008;14(4):454-8. doi: 10.1038/nm1692. Epub Mar. 16, 2008.
Liu et al., Hands-free, wireless goggles for near-infrared fluorescence and real-time image-guided surgery. Surgery. May 2011;149(5):689-98. doi: 10.1016/j.surg.2011.02.007.
Mahmood et al., Near-infrared optical imaging of protease activity for tumor detection. Radiology. Dec. 1999;213(3):866-70.
Pasternack et al., Highly sensitive size discrimination of sub-micron objects using optical Fourier processing based on two-dimensional Gabor filters. Opt Express. Jul. 6, 2009;17(14):12001-12.
Ramanujam et al., Fast and noninvasive fluorescence imaging of biological tissues in vivo using a flying-spot scanner. IEEE Trans Biomed Eng. Sep. 2001;48(9):1034-41.
Reinisch, Laser physics and tissue interactions. Otolaryngol Clin North Am. Dec. 1996;29(6):893-914.
Singletary et al., Revision of the American Joint Committee on Cancer staging system for breast cancer. J Clin Oncol. Sep. 1, 2002;20(17):3628-36.
Tung et al., In vivo imaging of proteolytic enzyme activity using a novel molecular reporter. Cancer Res. Sep. 1, 2000;60(17):4953-8.
Weissleder et al., In vivo imaging of tumors with protease-activated near-infrared fluorescent probes. Nat Biotechnol. Apr. 1999;17(4):375-8.
Weissleder et al., In vivo magnetic resonance imaging of transgene expression. Nat Med. Mar. 2000;6(3):351-4.
Yang et al., Presentation, 2010 IVIS Imaging System from Caliper LifeSciences, 104 slide presentation 52 pages.
Zaheer et al., In vivo near-infrared fluorescence imaging of osteoblastic activity. Nat Biotechnol. Dec. 2001;19(12):1148-54.
Zornig et al., Re-excision of soft tissue sarcoma after inadequate initial operation. Br J Surg. Feb. 1995;82(2):278-9.
Whitley et al., A mouse-human phase 1 co-clinical trial of a protease-activated fluorescent probe for imaging cancer. Cancer Imaging. 2016. 12 pages.

* cited by examiner

SYSTEM AND METHOD FOR THRESHOLDING FOR RESIDUAL CANCER CELL DETECTION

RELATED APPLICATIONS

This Application claims the benefit of priority under 35 U.S.C. 119(e) of U.S. Provisional Application Ser. No. 62/786,657, filed Dec. 31, 2018, the disclosure of which is incorporated herein by reference in its entirety.

BACKGROUND

More than one million cancer surgeries are performed each year in the United States and nearly 40% of them fail to remove the entire tumor according to the National Cancer Institute Surveillance Epidemiology and End Results report. Situations in which cancer cells were left behind in the patient can result in secondary surgeries. For example, in breast cancer lumpectomies, failure to remove all of the cancer cells during the primary surgery has been reported in literature to occur 15-40% of the time, which requires second surgeries. Such secondary surgery or multiple surgeries create increased rates of cancer recurrence and reduce long term survival of the patient.

Typically, after a solid tumor resection, the surgeon removes the bulk of the tumor and sends it to a pathologist for post-operative assessment of the resected tumor tissue to determine whether residual cancer was left behind in the patient. However, this pathology assessment is a time intensive procedure and often takes days for final results to be sent to the surgeon. Should the pathologist indicate in the pathology report finding of a portion of the removed tissue with cancer cells bordering the edge (a diagnostic term known as "positive margin"), additional resection may be required to complete removal of the residual cancer cells in the patient and in the situation after the patient has completed the initial surgery, this finding may require the surgeon to perform a second surgery.

SUMMARY

Various aspects of the present application relate to in situ observation of residual cancer cells in a tumor resection bed during cancer surgery. For example, there exists an imaging technology that includes a probe that fluoresces upon activation by a target cell and a hand-held fluorescence imaging device in order to allow for intraoperative identification of residual cancer in order to reduce the need for follow up surgeries and minimize the potential for recurrence. See, for example, U.S. patent application Ser. Nos. 14/211,201 and 14/211,259, the disclosures of which are incorporated herein by reference in their entirety. In situ observation techniques may typically provide an intraoperative surgical site image with cancer cells marked with an imaging agent against a background. The background of the surgical site image may include healthy tissues. Imaging the healthy tissues in the field of view of the surgical site image may facilitate the surgeon in locating the surgical site during operation, while the cancer cells highlighted with an imaging agent in the image may help the surgeon identify residual cancer to be removed. It is appreciated that there remains a need for detecting residual cancer cells during surgery in order to insure that all of the cancer has been removed from the tumor-bed.

The present application is directed to a method and system for performing image analysis for identification of residual cancer cells in a tumor resection bed. Further, the system and methods discussed herein may be used to detect pre-cancerous conditions as well. In particular, the present techniques are directed to determining a per-patient threshold used to determine whether images include (or are likely to include) healthy tissue or abnormal and/or cancerous tissue.

According to some embodiments, the techniques provide a system for determining a patient-specific threshold used to detect abnormal cells in a surgical site. The system includes a medical imaging device configured to produce a set of images of an anatomy of a patient. The system includes an image analysis system comprising one or more processors configured to receive the set of images, and analyze the set of images to determine a patient-specific threshold to use to detect abnormal tissue of the patient.

According to some embodiments, the techniques provide a computer-implemented method for determining a patient-specific threshold used to detect abnormal cells in a surgical site. The method includes receiving a set of images of an anatomy of a patient, and analyzing the set of images to determine a patient-specific threshold to use to detect abnormal tissue of the patient.

According to some embodiments, the techniques provide at least one non-transitory computer-readable storage medium comprising computer-executable instructions that, when executed by at least one processor of an image analysis system configured to collect a surgical site image, perform a method to calculate a threshold used to detect abnormal cells in a surgical site. The method includes receiving a set of images of an anatomy of a patient, and analyzing the set of images to determine a patient-specific threshold to use to detect abnormal tissue of the patient.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

The inventors have recognized and appreciated that in order to improve the efficacy of cancer surgeries, it is desirable to have a system that can identify from surgical site images abnormal cells such as residual cancer features that are mm to sub-mm in size and/or not easily identified with traditional visual inspection. Such techniques can use thresholding to determine whether one or more images collected from the patient's operating site contain abnormal and/or cancerous cells, and therefore may require further resection or removal. A set of initial images of the operating site can be acquired and used to generate a custom patient threshold. As explained herein, for example, the initial images can be summarized into representative intensity values and used to calculate the per-patient threshold. Prior techniques did not allow the image analysis system to be specifically fine-tuned for the particular patient. As discussed further herein, according to various aspects, various pixel analysis techniques are provided that analyze the pixels of the surgical site images and leverage statistical learning to further fine-tune the threshold calculation.

Figure 1:
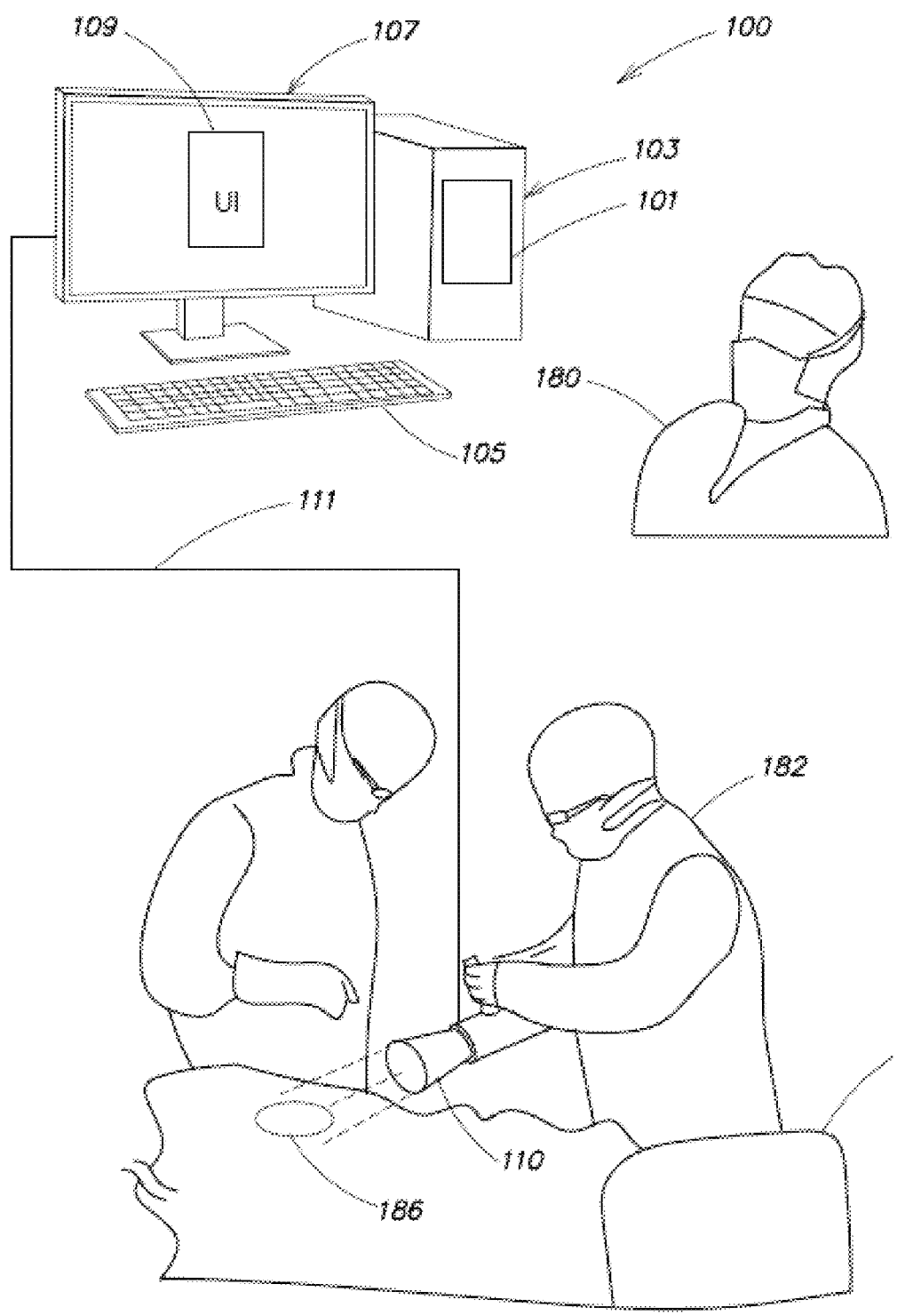
FIG. 1 is a schematic diagram showing an overview of components of an exemplary system for identifying residual cancer cells after surgery according to some embodiments.

FIG. 1 is a schematic diagram showing an overview of components of an exemplary system 100 for identifying residual cancer cells after surgery, according to an embodiment of the present application. An operator 180 may use one or more input devices 105 to interact with a User Interface (UI) 109 to issue commands and/or queries associated with an image analysis system 101. The image analysis system may be implemented using a computer-based hardware element 103 that is specially programmed to process one or more images in order to identify residual cancer features in the images. The output of the image analysis system may be presented on a display device 107 to the operator within the operating room environment.

In some embodiments, the images are captured of a patient's anatomy by one or more surgeons 182 during or after surgery on a patient on surgical bed 184. The patient's anatomy can include, for example, both internal and/or external structures of the patient's head, neck, thorax, abdomen, arms, hands, legs, feet, another appropriate structure, or some portion or combination thereof. The patient's anatomy may be an area where the surgeon is determining whether abnormal tissue may be present, such as a tumor, cancerous tissue, skin lesions, wounds, and/or any other structure that may include abnormal tissue. The images may be captured in-situ at the surgical site 186 where a tumor is resected using a medical imaging device and transmitted in real-time to the image analysis system 101 via a data connection 111. Used in this scenario, the system 100 is able to provide a real-time feedback on the size and location of residual cancer cells remaining in the surgical site after the resection surgery is performed. In some cases the image analysis results provided to the operator 180 may facilitate the surgeon 182 in performing residual cancer cell removal procedures on the patient and obtain further confirmation from the image analysis system that all remaining cancer cells in the surgical site 186 are completely removed, without the need for a second, separate residual cancer cell removal surgery.

Figure 2:
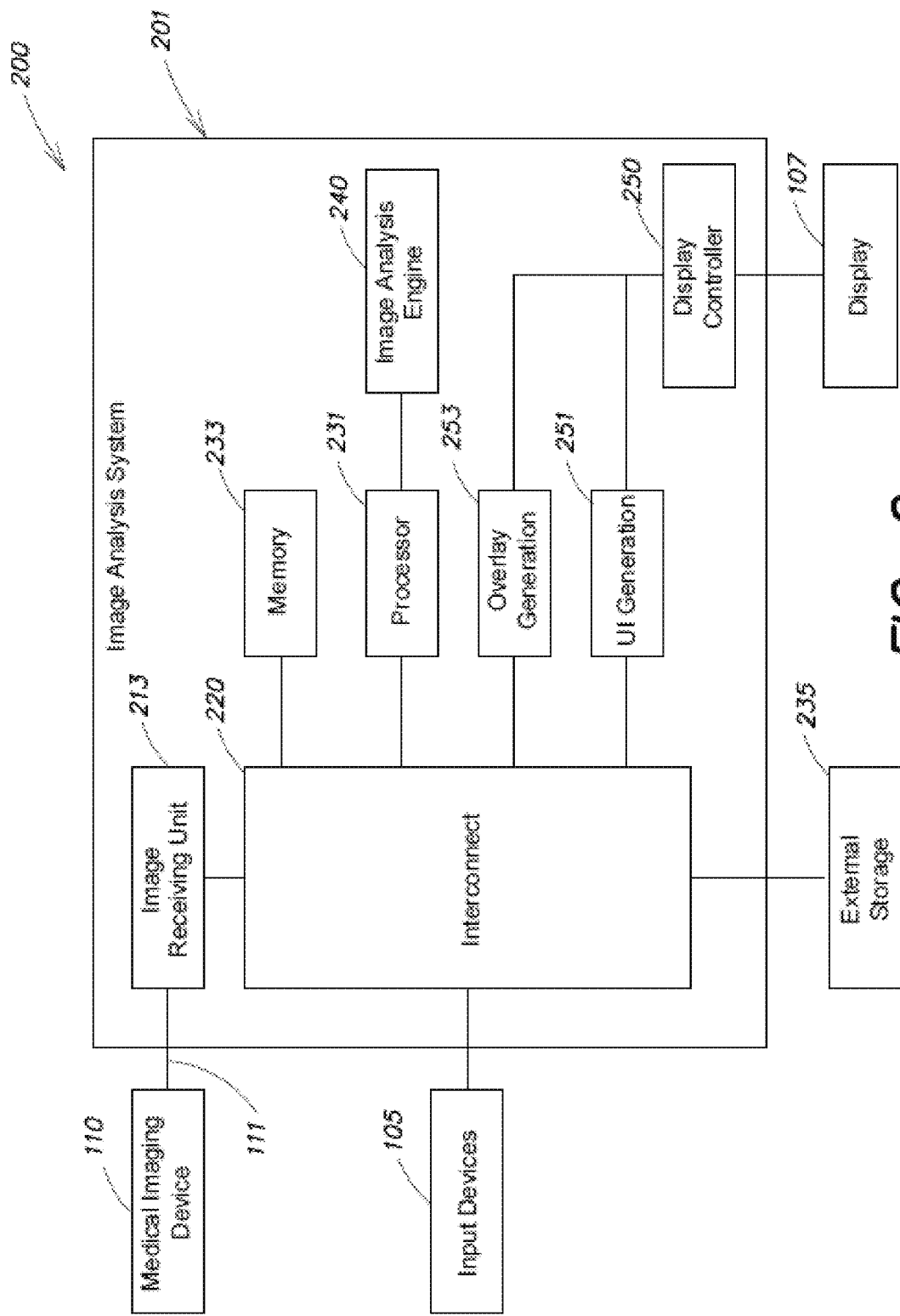
FIG. 2 is a block diagram of another exemplary cancer cell detection system according to some embodiments.

FIG. 2 is a block diagram of a cancer cell detection system 200 that is an example of the system 100 of FIG. 1. Some of the components are the same and thus the same reference numbers are used. In the example in FIG. 2, the image analysis system 201 includes an interconnect 220 used to interface with and coordinate with various different components in the system. The interconnect 220 may comprise one or more digital buses or any other type of suitable interconnections that allow high speed communication of digital data between a plurality of interconnected components. In some embodiments, the interconnect 220 interacts with processor 231 to process image data received from an image receiving unit 213 and obtains from the processor 231 the image analysis results in order to provide the image analysis results to an external display 107 for the operator 180. In some embodiments, the interconnect 220 may communicate non-image data with the processors. For example, processor 231 may receive programming instructions from the interconnect 220 in order to execute a series of methods on the processor. In some embodiments, the interconnect 220 communicates with a memory 233 to store and read image and non-image data for the processor. For example, memory 233 may be a computer memory that stores program instructions executable by the processor 231 that when executed by the processor 231, perform one or more methods to identify residual cancer cell features from images. It should be appreciated that any suitable computer readable storage media may be used in the image analysis system as memory 233 for storage of image data and program instructions.

According to some embodiments, processor 231 may additionally communicate with an image analysis engine 240 in order to process image data to identify residual cancer cell features. The image analysis engine 240 may include one or more units each specialized for executing instructions for image enhancement and analysis. Enhancing the image may help remove noise and artifacts unrelated to the cancer cell features and improve the signal noise ratio of the cancer cell signals against background. Image enhancement may be performed, for example, with one or more methods selected from the group comprising Canny Filtering, Sobel Filtering, Kayyali filtering, Principle Curvature-Based region detection, features from accelerated segment testing, Forstner filtering, a Laplacian of Gaussians, Tophat filtering, Difference of Gaussians, maximally stable extremum regions, and a determinant of Hessian.

In some embodiments, the units in image analysis engine 240 may be integrated on a single chip together with processor 231 in order to reduce packaging dimensions, power consumption and manufacturing cost. In some other embodiments, image analysis engine 240 may be implemented on discrete processing chips specialized in performing high speed image processing such as a graphics co-processor or a field programmable gate array (FPGA). Further, one or more image analysis features may be incorporated within the medical imaging device (e.g., device 110).

In the system in FIG. 2, display controller 250 receives the image analysis results from the processor 231 via interconnect 220 and provides one or more processed images indicating the size and location of the detected cancer feature to an external display 107 for the operator 180. In some embodiments, an overlay generation unit 253 generates an overlay and/or highlighting based on the image analysis results to be provided to the display controller such that the overlay and/or highlighting are presented to the operator 180 to accentuate the identified cancer features on the display 107.

In the system in FIG. 2, medical imaging device 110 is used to capture intraoperative images of the patient's surgical site and to transmit the captured image data to the image receiving unit 213 via a data connection 111. The captured image data may be stored in memory 233 and subsequently processed by processor 231 and image analysis engine 240 to identify residual cancer features in the image data. It should be appreciated that multiple image data may be captured by the medical imaging device, stored in memory 233 and processed by the processor 231 and image analysis engine 240 for output to display 107 in substantially the same period of time in order to provide real-time feedback of the size and location of residual cancer cells to the operator. For example, the medical imaging device 110 may capture images at a specific video rate (e.g., 10 frames per second, 12 frames per second, 24 frames per second or 30 frames per second) and transfer the video rate images for processing and output as real-time video features at substantially the same rate on display 107 in order to facilitate the surgeon's operation in removal of identified cancer cells.

In some embodiments, the medical imaging device 110 may be a handheld imaging device. In one non-limiting example, the handheld imaging device may be a hand-held fluorescence imaging device with a photosensitive detector sensitive to fluorescence signals corresponding to photons emitted from fluorescence of certain fluorescent imaging agent with which the cancer cells are labelled with. In some embodiments, the imaging device may also include an excitation source that is configured to emit excitation wavelengths of particular fluorescent imaging agent towards the object or surgical bed being imaged. A description of an example hand-held fluorescence imaging device may be found in U.S. patent application Ser. No. 14/211,201 titled "MEDICAL IMAGING DEVICE AND METHODS OF USE", filed on Mar. 14, 2014, the disclosure of which is incorporated herein by reference in its entirety. Of course, while a handheld device is mentioned above, the systems and methods described herein are not limited to only use with a handheld device. Instead, they may be implemented on any appropriate imaging and/or analysis system regardless of size scale.

According to some embodiments, images captured in a handheld imaging device may comprise pixels with brightness or intensity levels that correspond substantially to the number of fluorescent photons emitted from portions of tissues being imaged in the surgical site. The intensity value of each pixel on the captured image is substantially proportional to the number of fluorescently labelled cancer cells in a portion of the tissue within the total field of view of the imaging device. The size and location of a pixel relative to the captured image correspond to the size and location of the portion of the tissue relative to the total field of view in the imaging device. In some embodiments, the handheld imaging device may include a field of view of 2.5 cm, 1.3 cm, and/or other fields of view as can be appreciated by a person of skill in the art. Images transmitted from the medical imaging device 110 to the imaging receiving unit 213 may include a high number of pixels in each one of two orthogonal directions in an array, such that the size of the portion of the tissue corresponding to a pixel, or in other words the corresponding field of view for a single pixel, is no bigger than a size representing a desired spatial resolution of the imaging device. Without wishing to be bound by theory, a typical cancer cell may be on the order of approximately 15 μm across. The medical imaging device may be configured such that a field of view of each pixel may be equal to or greater than about 1 μm, 2 μm, 3 μm, 4 μm, 5 μm, 10 μm, 15 μm, 30 μm, or any other desired size. Additionally, the field of view of each pixel may be less than about 100 μm, 50 μm, 40 μm, 30 μm, 20 μm, 10 μm, or any other desired size scale.

In one specific embodiment, the field of view per pixel may be between about 5 μm and 100 μm inclusively. In another embodiment, the field of view per pixel may be between about 5 μm and 50 μm inclusively. Having the field of view of each pixel being on the same order in size or smaller than each cancer cell leads to enhanced resolution and contrast for labeled cancer cell features in the surgical site image, as each cancer cell is covered by one or more whole pixels with high fluorescent intensity against a background with much lower intensity. Such high resolution and contrast allows the system to identify small features with only a handful of cancer cells from surgical site images that are not easily identified with traditional visual inspection means. Of course pixels with fields of view both larger and smaller than those noted above are also contemplated, as the disclosure is not so limited. Further, such an imaging capability may permit detection of certain types of cancer cells having a particular shape and/or geometry. It is appreciated that particular cancer cells have a particular fundamental geometry and therefore such geometries may be stored in a memory, compared to sampled geometries and detected by the system.

In some embodiments, each image captured by the medical imaging device 110 comprises an array of pixels each with a digitized intensity value representing the concentration of imaging agents at the corresponding field of view of the pixel. In one example, the intensity value for each pixel is sampled and is digitized with 12-bit resolution. In other examples, the digitization resolution may be other resolutions such as 8-bit, 14-bit, 16-bit, or any suitable resolution for recording and transmitting the image. The captured images are transmitted from medical imaging device 110 to the image receiving unit 213 via data connection 111. In some embodiments, raw, uncompressed image data are transmitted to ensure integrity of the image, although it should be appreciated that any suitable data compression technique and format may be used to enhance the image data transmission rate from the medical imaging device 110.

Besides image data, the data connection 111 may also transmit non-image data from the medical imaging device 110 to the image analysis system 201. In one embodiment, image scaling information may be transmitted accompanying each surgical site image in order for the image analysis system to convert pixel size into units of length measurement such as mm or μm. In some embodiments, the converted sizes of one or more groups of pixels may be compared with a known threshold value based on cancer cell sizes and/or geometries in order to identify the one or more groups of pixels as cancer cells in the surgical site image.

Additionally, the data connection 111 may transmit non-image data from the image analysis system 201 to the medical imaging device 110. Such non-image data may be used, for example, by the operator 180 to control the medical imaging device to perform image capture, transmission, adjustment of magnification/total field of view and/or as focusing depth of the optical system within the medical imaging device to provide a full survey of the surgical bed for residual cancer cells after the initial tumor resection.

In some embodiments, operator 180 as shown in FIG. 1 may use one or more input devices 105 to interact with the image analysis system. In the embodiment in FIG. 2, input devices 105 are coupled to the interconnect 220 to route commands and queries from the operator to various components of the system. The input devices may include a keyboard for typing text, a mouse to interact with one or more screen objects on the UI 109 on the display 107 as shown in FIG. 1. For example, the operator may type in annotation texts accompanying the received surgical site image or the analyzed residual cancer cell results. The operator may use the input device to reconfigure the UI 109, interact with UI 109 to adjust settings on the medical imaging devices and/or image analysis settings such as one or more threshold values depending on the type of cancer cells being treated. In some embodiments the input devices may also include a stylus-sensitive or a finger-sensitive touch screen, external or integral to the display 107. It should be appreciated that any suitable human interface device may be used for the operator 180 to provide commands and queries to the system. In some embodiments the input devices may include gesture controls or voice controls. In another embodiment, the input devices may additionally provide audio, visual or tactile feedback to the operator to indicate one or more characteristics in relation to the input command and/or queries.

In some embodiments, the image analysis system 201 in FIG. 2 may include a UI generation engine 251 adapted to generate screen objects for the display controller 250 to present on the display 107 as the UI for interacting with the operator. The UI may be generated based on instructions stored in memory 233 and may be dynamically adjusted based on user input from input devices 105.

The system 200 in FIG. 2 may also include external storage 235 connected to the interconnect 220, configured to store both image data and non-image data, for example, for archival purpose. In some embodiments, program instructions may be read from and stored on the external storage 235.

As discussed above, aspects of the present application relate to methods for detecting cancer cells, such as those remaining in a surgical site after removal of bulk tumors, in order to facilitate complete removal of residual cancer cells. In particular, aspects relate to a thresholding algorithm that determines a threshold used in the cancer cell detection process that is tailored to each patient. As a general introduction not intended to be limiting, the techniques can include one or more of the following steps. The techniques discuss an exemplary order for clarity, but can be implemented using a different order and/or combination of steps. First, images of the surgical site can be processed (e.g., background correction and/or flattening). Second, the techniques can search for regions above a threshold based on normal tissue. Third, it can be determined whether feature(s) are above a lower size threshold. If a feature meets the second and third steps, then the feature is highlighted. Fourth, if no feature exists, contrast enhancement can be used to modify all or a portion of the image. Fifth, the techniques can search for features above a certain threshold in the contrast-enhanced figure. Sixth, it can be determined whether that feature meets one or more criteria, such as size and contrast criteria. If a feature meets the fifth and sixth steps, then the feature is highlighted.

Figure 3:
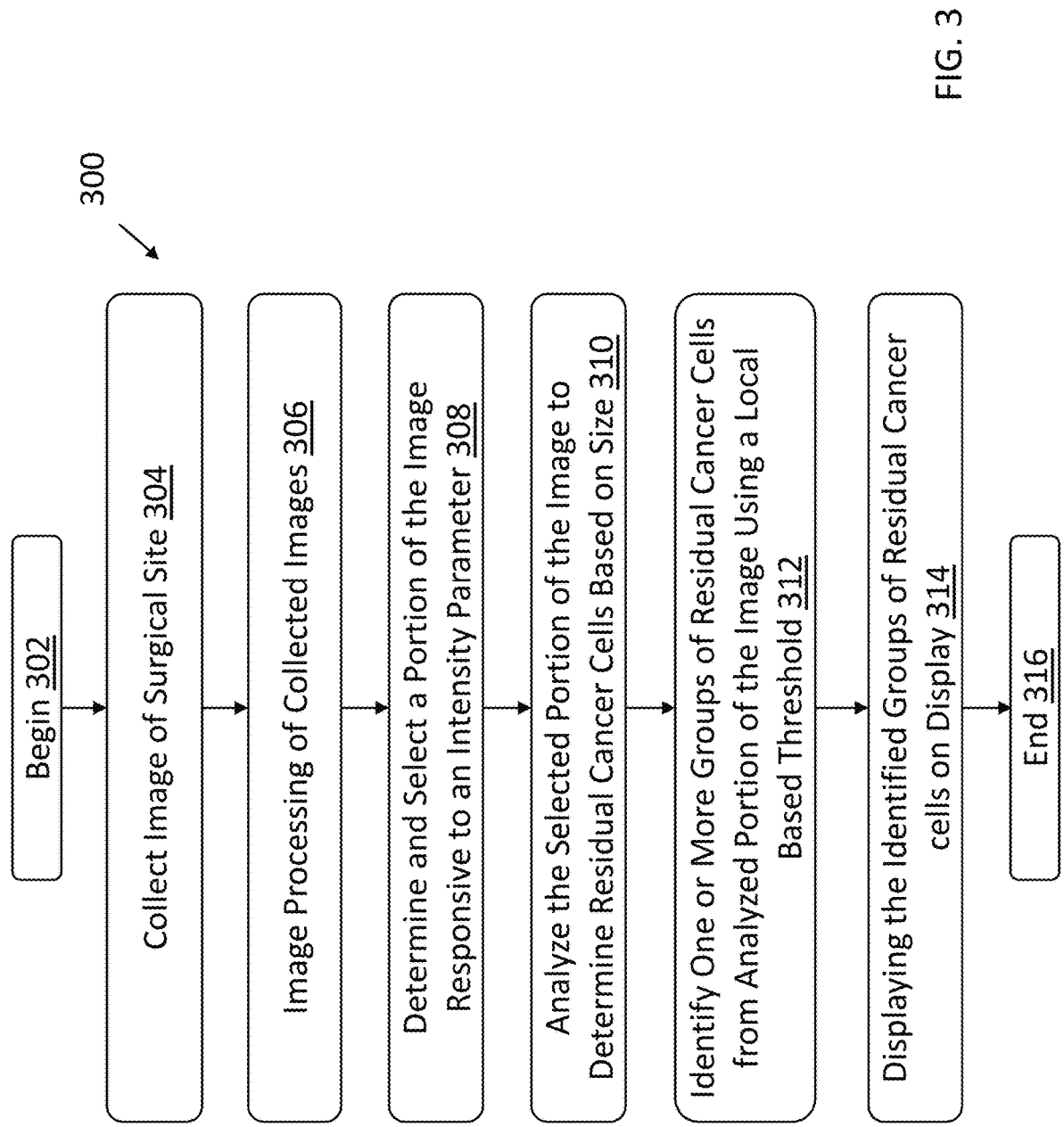
FIG. 3 is a flow chart showing an exemplary process for detecting residual cancer cells according to some embodiments.

FIG. 3 is a flow chart showing an exemplary process 300 for detecting residual cancer cells according to some embodiments. After the process begins at block 302 in FIG. 3, at block 304, images are captured at the surgical site using, for example, a handheld imaging device as discussed above. In some embodiments, the surgical site images may be still images and/or videos containing images captured at a particular video rate. At block 306, an image enhancement process may optionally and additionally be performed to enhance the images collected at block 304 in process 300.

At block 308, a portion of the collected image is selected based on a comparison between a characteristic of the pixels in the portion of the image with a predetermined characteristic threshold. In one non-limiting example, the portion of the image may be selected for further analysis after a determination that the intensity parameter for each pixel in the portion of the image exceeds a threshold value corresponding to a simple brightness threshold expected for a given type of cancer cell labeled with an imaging agent. One exemplary goal for performing a selection process based on thresholding can be to exclude background pixels representing light emission from healthy tissues from further analysis. The inventors have recognized that in some embodiments, even though fluorescent imaging agents are configured to selectively bind to cancer cells, finite fluorescence intensity may still appear in pixels corresponding to non-cancer cell regions in the surgical site. As discussed further herein, the techniques can include one or a plurality of thresholding steps that apply a threshold to the pixels. For example, feature detection (e.g., small cell feature detection) can include a first thresholding step that applies a threshold to the image(s) (e.g., processed image(s)), and a second thresholding step that applies a threshold to (e.g., local) features in the original image(s) that fall above the threshold in the first thresholding step.

In some cases, the finite background intensity may be due to background noise in the photodetector or in the circuitry of the medical imaging device. The finite background intensity may also arise from fluorescent signals emitted from a small amount of imaging agents with non-specific binding in the healthy, non-cancer cell regions. Therefore in some embodiments, relying on a simple threshold determination alone may not be sufficient to prevent false positive identification of cancer cell regions, weed out background tissues and accentuate substantially only cancer cells from the images.

Subsequently at block 310, the portion of the collected image selected at block 308 is analyzed to identify one or more groups of residual cancer cell features against background based on size. For example, features in the selected portion of the image may be discarded or excluded if representative sizes of the features are determined to be outside a size range associated with the cancer cell type targeted for removal. As used herein, feature size should be understood to refer to a properly scaled size dimension of a region of tissues on the surgical site as measured in, e.g., mm or µm, that corresponds to the feature on the surgical site image.

At block 312, the one or more groups of residual cancer cells identified at block 310 are further filtered using a local based contrast method, as will be discussed in detail below. In some embodiments, a local contrast is determined for each group of residual cancer cell features based on a comparison between signal intensity of pixels substantially within and outside the feature. Only features with contrast above a predetermined threshold are identified as cancer cells in order to distinguish against the background and reduce false positive identifications.

The identified cancer cells according to blocks 308, 310 and 312 are presented to a display (such as display 107 in FIG. 1) to operator 180 at block 314 before the residual cancer cell identification process ends at block 316.

In some embodiments, each of the process blocks 308 to 312 and 306 as illustrated in the block diagram in FIG. 3 may be applied individually or selectively in groups of any suitable combination sequence depending on the type of tissue and/or residual cancer cell types being targeted.

In some embodiments, the exemplary process 300 shown in FIG. 3 may be performed by the system 200 in FIG. 2 sequentially to process images received by the image receiving unit 213 from the medical imaging device.

For example, according to one embodiment, the system may be adapted to detect particular cancer and pre-cancerous cells. In one embodiment, the system may store parameters indicating particular size and geometries of certain indicated cancers and pre-cancerous indications including, but not limited to invasive ductal carcinoma, invasive lobular carcinoma, ductal carcinoma in situ, ovarian cancer, metastatic ovarian cancer, brain metastases, peritoneal carcinomatosis, esophageal cancer, Barrett's esophagus, colorectal polyps, colorectal cancer, melanoma, basal cell skin cancer, squamous cell skin cancer, prostate cancer, lung cancer, sarcoma, endometrial hyperplasia, endometrial cancer, and cervical dysplasia, among other types.

As shown in block 312 of method 300, the threshold can be an important aspect of the detection process, because the image analysis system uses the threshold to determine whether (or not) an image includes residual cancer cells. In some embodiments, the portion of the image selected in block 308 can be based on the brightest contiguous feature in the image. For example, the image analysis system can select a circle of a particular diameter (e.g., 500 um, 1000 um) around the area with the brightest contiguous feature. The image analysis system can use the pixels in the selected area to compare the associated feature to the threshold. For example, the image analysis system can compare the lowest pixel intensity value in the selected area to the threshold to make an automatic determination of whether the associated feature in the image contains abnormal tissue (e.g., cancerous tissue,) that require further resection. This is referred to as the TB1000 um below.

Figure 4:
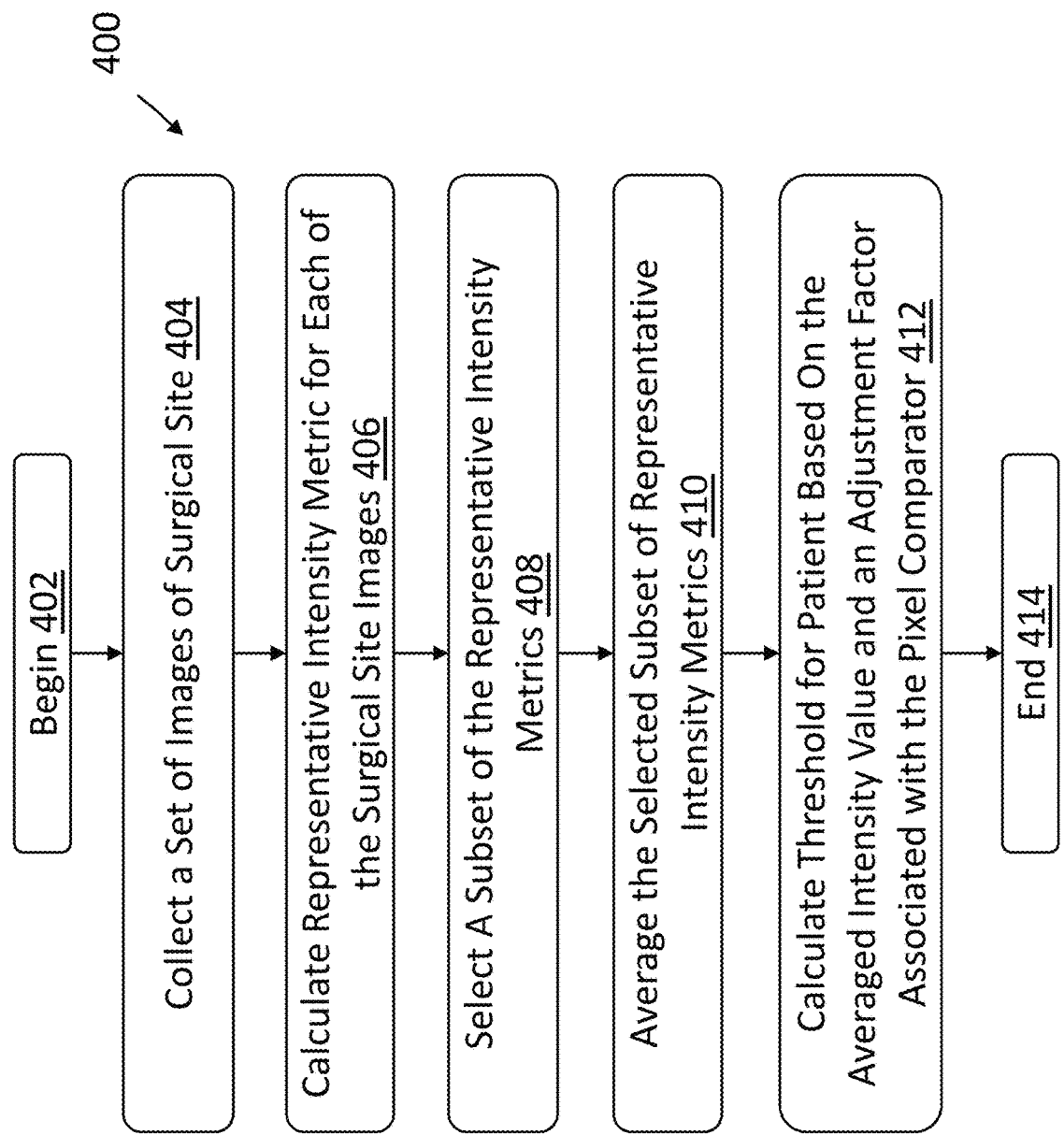
FIG. 4 is a flow chart showing an exemplary process for calculating a patient-specific threshold according to some embodiments.

FIG. 4 is a flow chart showing an exemplary process 400 for calculating a patient-specific threshold according to some embodiments.

The process 400 begins at block 402. At block 404, the medical imaging device (e.g., the medical imaging device 110 in FIG. 1) produces a set of surgical site images for a patient. Generally, at blocks 406-412, an image analysis system (e.g., the image analysis system 101 in FIG. 1) collects and analyzes the set of surgical site images collected at block 404 to determine a patient-specific threshold that can be used to detect abnormal tissue for the patient (e.g., using new images captured of the patient's surgical site using the medical imaging device). In some embodiments, the set of surgical site images are images of healthy tissue. However, embodiments, in which the images are images of abnormal tissue and/or images including both healthy and abnormal tissue are also contemplated.

At block 406, the image analysis system calculates, using a pixel comparator, a representative intensity metric for each surgical site image collected at step 404 to generate a set of representative intensity metrics. The representative intensity metric represents the pixel intensity values of the associated image. The pixel comparator can be, for example, a mean comparator, a percentile comparator, a fixed comparator, and/or other statistical comparator, as discussed further herein. For example, in some embodiments the comparator can be a means comparator, and the representative intensity metric can be the means of the pixel intensity values of the associated image, as discussed further herein.

At block 408, the image analysis system selects a subset of the set of representative intensity metrics based on a predetermined criterion. In some embodiments, the predetermined criterion is used to filter out one or more of the representative intensity metrics in the set of representative intensity metrics. For example, the image analysis system may be configured to select, for a particular comparator, a certain number of the lowest values of the representative intensity metrics, as discussed further herein.

At block 410, the image analysis system averages the selected subset of representative intensity metrics to calculate an averaged intensity value.

At block 412, the image analysis system calculates the threshold for the patient based on the averaged intensity value and an adjustment factor associated with the pixel comparator. For example, the adjustment factor may be a multiplier that is used to multiply the averaged intensity value to determine the threshold. The process ends at block 414. Once calculated, the threshold can be used by the image analysis system to detect abnormal cells for the particular patient.

Referring to block 406, the image analysis system uses a pixel comparator to calculate the representative intensity metric for each surgical site image. In some embodiments, the comparator is a maximums comparator that calculates the representative intensity value for each surgical site image by calculating a maximum pixel intensity value of each surgical site image. In some embodiments, the comparator is a minimums comparator that calculates the representative intensity value for each surgical site image by calculating a minimum pixel intensity value of each surgical site image. In some embodiments, the comparator is a means comparator that calculates the representative intensity value for each surgical site image by calculating a mean of pixel intensity values of the surgical site image. In some embodiments, the comparator is a twenty-fifth percentile comparator that calculates the representative intensity value for each surgical site image by calculating a 25th percentile of pixel intensity values of the surgical site image. In some embodiments, the comparator is a fixed comparator that uses a fixed threshold. The threshold can be calculated using, for example, the Youden point on an ROC (e.g., an ROC in which no patient-specific comparator statistic was used). In some embodiments, the fixed threshold can be the same for all patients and/or a subset of patients. In some embodiments, the comparator is a medians comparator that calculates the representative intensity value for each surgical site image by calculating the median pixel intensity value for each image.

Referring to block 408, the image analysis system selects a subset of the set of representative intensity metrics based on a predetermined criterion. For example, the image analysis system may select a certain number of the representative intensity metrics, such a certain number of the highest metrics, or a certain number of the lowest metrics. For example, if block 404 collects six images of the surgical site, at block 406 the image analysis system can be configured to calculate six different representative intensity metrics (e.g., means, or $25^{th}$ percentiles), one for each image. The predetermined criterion can cause the image analysis system to select, for example, a certain number of the lowest representative intensity values. For example, if block 404 collects six images, the predetermined criterion can cause the image analysis system to select all six representative intensity values, five of the representative intensity values, four of the values, and so on, down to two or even one of the representative intensity values). For example, a lowest six mean comparator can be associated with a predetermined criterion that selects the lowest six of the representative intensity values calculated for the set of collected images using a means function. As another example, the a lowest two mean comparator can be associated with a predetermined criterion that selects the lowest two of the representative intensity values calculated for the set of collected images using a means function. As a further example, the predetermined criterion can cause the image analysis system to perform an average of various comparators, such as an average of the second and third lowest cavity initialization image means. In some embodiments, the predetermined criterion is associated with the comparator (e.g., a particular comparator, such as a means comparator, is associated with a predetermined criterion that identifies how to select the subset of representative intensity metrics).

Referring to block 410, the image analysis system averages the selected subset of representative intensity metrics to calculate an averaged intensity value. In some examples, the image analysis system computes a traditional average by summing the representative intensity metrics and dividing the sum by the number of representative intensity metrics. A person of skill in the art will appreciate that other techniques can be used to combine the representative intensity metrics into an averaged intensity value. For example, root mean square, geometric mean, median, sum, and/or the like can be used to combine the representative intensity metrics.

Referring to block 412, the image analysis system calculates the threshold for the patient based on the averaged intensity value computed in block 410. The image analysis system can also use an adjustment factor associated with the pixel comparator to calculate the threshold. For example, the adjustment factor can be a multiplier that is associated with the pixel comparator (e.g., a multiplier with a whole number value or fractional value ranging from 1.0 to 25, such as from 1.0 to 3.5, from 18 to 21, and/or the like). Each pixel comparator can be associated with the same and/or a different multiplier. As discussed above in conjunction with step 408, each comparator can be associated with a predetermined criterion. A person of skill will appreciate that the comparators and adjustment factors discussed herein are for exemplary purposes only and are not intended to be limiting.

Once the image analysis system calculates the threshold, the image analysis system can use the threshold to identify residual abnormal cells in images of the patient's surgical site. For example, the process 300 described in conjunction with FIG. 3 can be used to analyze the patient's surgical site, where the calculated threshold is used in block 312 to identify one or more groups of residual cancer cells.

Figure 5:
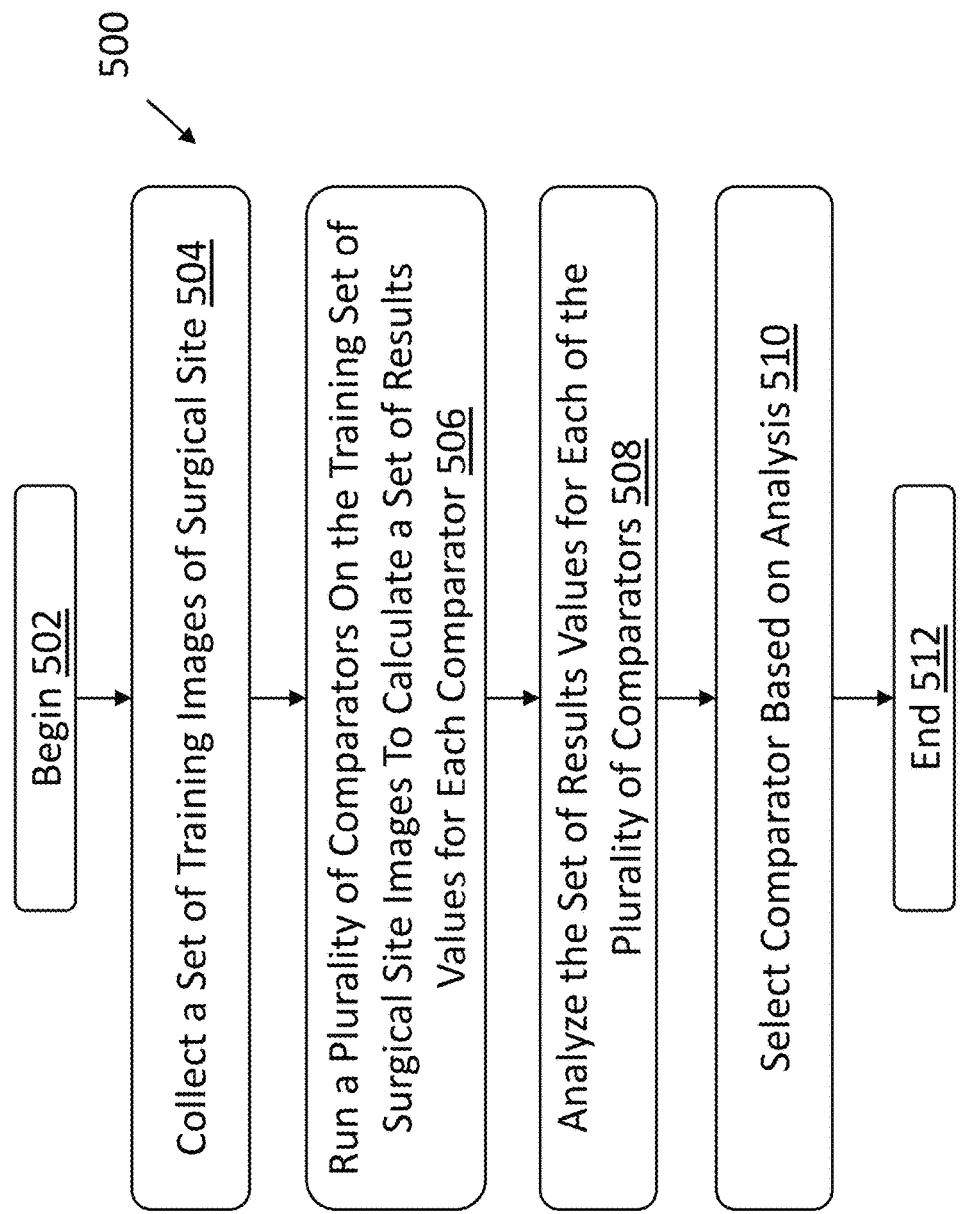
FIG. 5 is a flow chart showing an exemplary process for selecting a comparator according to some embodiments.

FIG. 5 is a flow chart showing an exemplary process 500 for selecting a comparator to use for the threshold calculation according to some embodiments. The process 500 begins at block 502. At block 504, the medical imaging device collects a set of training images of the patient's surgical site. At block 506, the image analysis system runs a plurality of comparators (e.g., means comparators, percentile comparators, fixed comparators, etc.) on a training set of surgical site images to calculate a set of results values for each of the comparators. At block 508, the image analysis system analyzes the set of results values for each of the plurality of comparators. At block 510, the image analysis system selects the comparator from the plurality of comparators based on the analysis performed at block 508. The process 500 terminates at block 512. As discussed in conjunction with FIG. 4, the selected comparator can be used to calculate the patient threshold.

Referring to block 504, in some embodiments the set of training images can be of a particular patient's surgical site, and/or of a group of patients. For example, surgical site images can be collected from a set of patients. In some embodiments, the patients can be pre-processed such that patients are excluded for various reasons, such as due to imaging time outside of a recommended imaging window. For each patient, a predetermined number (e.g., two, six, ten, etc.) of cavity initialization images can be generated following removal of the gross lump. Additional images, image processing, and/or surgical procedures can be performed to refine the data set. For example, the image analysis system can generate oriented images of the first surgical cavity. Standard of care shaves can be removed after each orientation is imaged, and additional images can be generated and used to assess whether additional tissue should be removed. For the assessment of whether additional tissue can be used, the normal tissue threshold can be periodically re-optimized during the data collection procedure. Following a surgery, histopathology can be used to determine whether an image actually contained residual cancer.

Referring to block 506, once the full data set is collected in block 504, the image analysis system runs a plurality of comparators on the training set of surgical site images to calculate a set of results values for each of the comparators. The system can be configured to run one or more analyses of the comparators to determine the results values. The set of results values can include, for example, Receiver Operating Characteristic (ROC) curves. A person of skill will appreciate that a ROC curve is a graphical plot that illustrates the diagnostic ability of a classifier system (e.g., abnormal and/or cancerous cells, or not) as its discrimination threshold (e.g., the threshold discussed herein) is varied. The ROC statistics can include, for example, the full ROC Area Under the Curve (AUCs), AUCs after leave one out (LOO) cross validation (e.g., referred to as AUC LOO), and/or the like. The AUC is a summary statistic that represents, in general, the probability that a classifier will rank a randomly chosen positive instance higher than a randomly chosen negative instance. A person of skill will appreciate that LOO cross validation is a model validation technique used to assess how the results of a statistical analysis will generalize to an independent data set, where one observation is used as the validation set and the rest are used as the training set. While the techniques described herein can be configured to use ROC and LOO cross validation, a person of skill will appreciate that other statistical techniques can be used without departing from the spirit of the techniques described herein.

The set of results values can include results values determined based on a Youden index. The Youden index is defined for all points of the ROC curve, which has a value ranging from −1 to 1 (where 0 is a useless test, and 1 is the ideal test). For example, the results values can include optimized Youden points for each AUC. Additionally, or alternatively, the results values include Wilcoxon results. A person of skill will appreciate that a Wilcoxon rank-sum test is a test that can be used to determine whether two independent samples were selected from populations having the same distribution. For a given comparator, the techniques can scan the value that is multiplied by that comparator to get an ROC. The multipliers can be calculated, for example, by determining which gives the highest Youden point.

In some embodiments, the set of results values can include for each comparator the number of true negative results, true positive results, false negative results, false positive results, and/or some combination thereof. The exemplary results values can include a sensitivity value, a specificity value, or both. In some examples, for each comparator the results values (e.g., statistics) can be calculated for that comparator at its Youden point.

In some embodiments, the full data set used to calculate the results values, e.g., after normalization by a given thresholding value, can be broken up into cancer positive and cancer negative populations. These two separate positive and negative populations can be evaluated for normality by assessing the goodness of fit to a log normal distribution. The log normal distributions for normal tissue-containing and cancer tissue-containing images can be used to generate a parameterized ROC curve. The best optimized Youden point from the parameterized ROC curves can be used to select the comparator and related aspects (e.g., predetermined criterion and adjustment factor).

In some embodiments, other comparators can be used in addition to, or in place of, the means and percentiles comparators. The image means and percentiles may be chosen to represent normal tissue because they are robust and/or statistically efficient. For example, the mean comparator may incorporate more pixel values from each image, which can result in a higher likelihood of arriving at a number that represents normal tissue for a given patient (e.g., compared to other comparators). As another example, the percentile (e.g., $25^{th}$ percentile) may avoid pixels that might include abnormal tissue or tumor, which could artificially raise the threshold and lead to false negatives. In some examples, a fixed comparator that uses a fixed threshold may not comprehend patient to patient variations in image signals.

In some embodiments, cross validations are used to determine the results values. For example, cross validations can be used to assess how well a statistical model will translate to an independent data set (e.g., a different data set other than that used to train the model, such as a real-time data set captured during a surgical procedure). For example, a cross validation can be used to define a data set to test the model during the training phase, in order to avoid problems such as overfitting. Such validations can be used for predictive modelling. In some embodiments, LOO cross validations can be performed for each comparator as discussed above, in which one of the observations (e.g., images and/or associated values) is used as the validation set, and the remaining observations are used as the training set. For example, each value (e.g., single image) in the set of images can be iteratively excluded, with the remaining values being used as a training set. In some examples, these values can be fit using a logistic regression, and the output of the logistic regression can be used to determine the probability of the excluded value being either pathology positive or negative. Hence, for each iteration, an excluded value can act as a validation set and receives a probability value. The array of probabilities for excluded values along with corresponding pathology values can be used to generate ROCs and their AUC values.

Referring to block 508, in some embodiments the image analysis system can analyze the set of results values by comparing AUC's for the full data set, the LOO cross validation, and/or both. For example, if the image analysis system compares the AUCs and determines that a particular percentage decrease is observed for a comparator (e.g., if there is a larger than 5% decrease in AUC and/or AUC LOO), then the comparator can be excluded from consideration for use in calculating the threshold. For example, such a comparator can be excluded based on the notion that the AUC of the full data set is a poor predictor of future performance.

In some embodiments, the data can be evaluated for normality to refine the comparator results values. For example, after conducting an initial survey of thresholding approaches on a data set (e.g., set of images for different patients), the data can be evaluated for normality, such as by fitting the data to a log normal distribution. The normality of a data set can be assessed based on the linearity of a normal probability plot.

In some embodiments, results values can be calculated for the comparators without analyzing the data set for outliers. In some embodiments, normal probability plots of the natural log of the ratio of TB1000 um (as discussed above, the minimum value in a 1000 um diameter circle around the brightest contiguous feature in the image) to normalizer values can be computed for both normal and cancer-tissue containing images to search for outliers in the training data set. In some embodiments, following exclusion of image outliers, the comparator survey can be recalculated to determine updated results values. In some embodiments, the image analysis system evaluates the comparators with the best Youden points. In some embodiments, the comparators can be evaluated using a parametric model.

Figure 6:
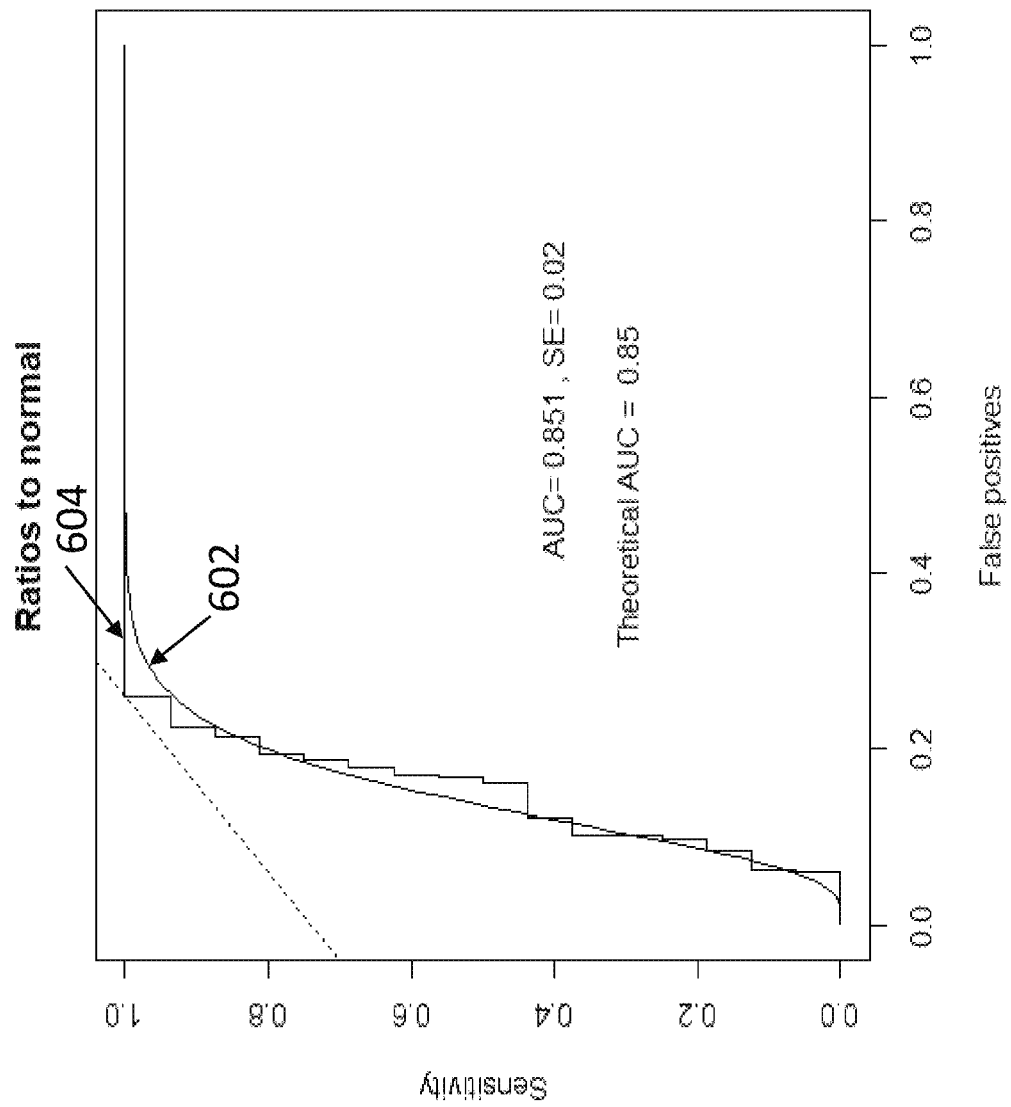
FIG. 6 is a plot of exemplary parametric and non-parametric Receiver Operating Characteristics (ROCs) for a lowest 2 mean comparator according to some embodiments.

FIG. 6 is a plot of exemplary parametric and non-parametric ROCs for a comparator according to some embodiments. In FIG. 6, the x-axis is false positives ranging from 0-1, and the y-axis is the sensitivity ranging from 0-1. The parametric ROC is shown as 602, and the non-parametric ROC is shown as 604. In some examples, such a similarity can confirm the visual goodness of fit.

Referring to block 510, the image analysis system selects the comparator from the plurality of comparators based on the analysis performed at block 508. As discussed in conjunction with block 506, after analyzing the results values, system can select the top performing comparator. In some embodiments, the image analysis system can perform further statistical analysis of the selected comparator. For example, in some embodiments, the image analysis system performs a Wilcoxon Rank-Sum test on the data set (e.g., the data set used to generate the results values for the comparators) using the selected comparator.

Depending on the nature of the computing device, one or more additional elements may be present. For example, a smart phone or other portable electronic device may include a camera, capable of capturing still or video images. In some embodiments, a computing device may include sensors such as a global positioning system (GPS) to sense location and inertial sensors such as a compass, an inclinometer and/or ran accelerometer. The operating system may include utilities to control these devices to capture data from them and make the data available to applications executing on the computing device.

As another example, in some embodiments, a computing device may include a network interface to implement a personal area network. Such an interface may operate in accordance with any suitable technology, including a Bluetooth, Zigbee or an 802.11 ad hoc mode, for example.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present application are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present application can be implemented in any of numerous ways. For example, the disclosed method may be applied to imaging methodologies beyond simple fluorescence, including MRI, Ultrasound, Mammography and other X-ray techniques, Raman, Two-Photon Microscopy and others.

For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format. In the embodiment illustrated, the input/output devices are illustrated as physically separate from the computing device. In some embodiments, however, the input and/or output devices may be physically integrated into the same unit as the processor or other elements of the computing device. For example, a keyboard might be implemented as a soft keyboard on a touch screen. Alternatively, the input/output devices may be entirely disconnected from the computing device, and functionally integrated through a wireless connection.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present application as discussed above. As used herein, the term "computer-readable storage medium" encompasses only a computer-readable medium that can be considered to be a manufacture (i.e., article of manufacture) or a machine. Alternatively, or additionally, the invention may be embodied as a computer readable medium other than a computer-readable storage medium, such as a propagating signal.

The terms "code", "program" or "software" are used herein in a generic sense to refer to any type of computer code or set of computer-executable instructions that can be employed to program a computer or other processor to implement various aspects of the present application as discussed above. Additionally, it should be appreciated that according to one aspect of this embodiment, one or more computer programs that when executed perform methods of the present application need not reside on a single computer or processor, but may be distributed in a modular fashion amongst a number of different computers or processors to implement various aspects of the present application.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present application may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A system for determining a patient-specific threshold used to detect abnormal cells, the system comprising:
   a medical imaging device configured to produce a set of fluorescence images of an anatomy of a patient; and
   an image analysis system comprising one or more processors configured to:
      receive the set of fluorescence images; and
      analyze the set of fluorescence images to determine a patient-specific threshold to use to detect abnormal tissue of the patient,
   wherein the image analysis system is configured to:
      analyze the set of fluorescence images by calculating, using a pixel comparator, one or more representative intensity values for each fluorescence image in the set of fluorescence images that represents one or more pixel intensity values of the associated fluorescence image to generate a set of representative intensity values,
      select a subset of the set of representative intensity values corresponding to the set of fluorescence images based on a predetermined criterion that is used to filter out one or more of the representative intensity values in the set of representative intensity values;
      average the selected subset of representative intensity values to calculate an averaged intensity value; and
      calculate the patient-specific threshold based on the averaged intensity value and an adjustment factor associated with the pixel comparator.

2. The system of claim 1, wherein the fluorescence images are surgical site fluorescence images of a surgical site of the patient.

3. The system of claim 2, wherein:
   the medical imaging device is configured to produce a new surgical site fluorescence image;
   the image analysis system is further configured to identify one or more groups of abnormal cells in the new surgical site fluorescence image based on the calculated patient-specific threshold; and
   the system comprises a display configured to indicate one or more locations of at least one of the one or more groups of identified abnormal cells.

4. The system of claim 1, wherein the pixel comparator is selected from the group consisting of:
   a maximums comparator that calculates the one or more representative intensity values for each fluorescence image in the set of fluorescence images by calculating a maximum pixel intensity value of each fluorescence image;
   a minimums comparator that calculates the one or more representative intensity values for each fluorescence image in the set of fluorescence images by calculating a minimum pixel intensity value of each fluorescence image;
   a means comparator that calculates the one or more representative intensity values for each fluorescence image in the set of fluorescence images by calculating a mean of pixel intensity values of each fluorescence image;
   a twenty-fifth percentile comparator that calculates the one or more representative intensity values for each fluorescence image in the set of fluorescence images by calculating a 25% percentile of pixel intensity values of each fluorescence image; and
   a medians comparator that calculates the one or more representative intensity values for each fluorescence image in the set of fluorescence images by calculating a median pixel intensity value for each fluorescence image.

5. The system of claim 1, wherein the image analysis system is configured to select the pixel comparator from a plurality of pixel comparators, comprising:
   running the plurality of pixel comparators on a training set of images to calculate a set of results values for each of the pixel comparators in the plurality of pixel comparators;
   analyzing the set of results values for each pixel comparator in the plurality of pixel comparators; and
   selecting the pixel comparator from the plurality of pixel comparators based on the analysis.

6. The system of claim 1, wherein each fluorescence image in the set of fluorescence images is an image of healthy tissue.

7. The system of claim 1, wherein the adjustment factor is a multiplier.

8. The system of claim 7, wherein the multiplier ranges from 1 to 25.

9. A computer-implemented method for determining a patient-specific threshold used to detect abnormal cells, the method comprising:

receiving a set of fluorescence images of an anatomy of a patient; and analyzing the set of fluorescence images to determine a patient-specific threshold to use to detect abnormal tissue of the patient, wherein analyzing the set of fluorescence images comprises:

calculating, using a pixel comparator, one or more representative intensity values for each fluorescence image in the set of fluorescence images that represents one or more pixel intensity values of the associated fluorescence image to generate a set of representative intensity values, selecting a subset of the set of representative intensity values corresponding to the set of fluorescence images based on a predetermined criterion that is used to filter out one or more of the representative intensity values in the set of representative intensity values;

averaging the selected subset of representative intensity values to calculate an averaged intensity value; and calculating the patient-specific threshold based on the averaged intensity value and an adjustment factor associated with the pixel comparator.

10. The method of claim 9, wherein the fluorescence images are surgical site fluorescence images of a surgical site of the patient.

11. The method of claim 10, further comprising:
receiving a new surgical site fluorescence image;
identifying one or more groups of abnormal cells in the new surgical site fluorescence image based on the calculated patient-specific threshold; and
indicating, via a display, one or more locations of at least one of the one or more groups of identified abnormal cells.

12. The method of claim 9, wherein the pixel comparator is selected from the group consisting of:

a maximums comparator that calculates the one or more representative intensity values for each fluorescence image in the set of fluorescence images by calculating a maximum pixel intensity value of each fluorescence image;

a minimums comparator that calculates the one or more representative intensity values for each fluorescence image in the set of fluorescence images by calculating a minimum pixel intensity value of each fluorescence image;

a means comparator that calculates the one or more representative intensity values for each fluorescence image in the set of fluorescence images by calculating a mean of pixel intensity values of each fluorescence image;

a twenty-fifth percentile comparator that calculates the one or more representative intensity values for each fluorescence image in the set of fluorescence images by calculating a 25% percentile of pixel intensity values of each fluorescence image; and a medians comparator that calculates the one or more representative intensity values for each fluorescence image in the set of fluorescence images by calculating a median pixel intensity value for each fluorescence image.

13. The method of claim 9, further comprising selecting the pixel comparator from a plurality of pixel comparators, comprising:

running the plurality of pixel comparators on a training set of images to calculate a set of results values for each of the pixel comparators in the plurality of pixel comparators;

analyzing the set of results values for each pixel comparator in the plurality of pixel comparators; and selecting the pixel comparator from the plurality of pixel comparators based on the analysis.

14. The method of claim 9, wherein each fluorescence image in the set of fluorescence images is an image of healthy tissue.

15. The method of claim 9, wherein the adjustment factor is a multiplier.

16. The method of claim 15, wherein the multiplier ranges from 1 to 25.

17. At least one non-transitory computer-readable storage medium comprising computer-executable instructions that, when executed by at least one processor of an image analysis system configured to collect one or more fluorescence images, perform a method to calculate a threshold used to detect abnormal cells, the method comprising:

receiving a set of fluorescence images of an anatomy of a patient; and analyzing the set of fluorescence images to determine a patient-specific threshold to use to detect abnormal tissue of the patient, wherein analyzing the set of fluorescence images comprises:

calculating, using a pixel comparator, one or more representative intensity values for each fluorescence image in the set of fluorescence images that represents one or more pixel intensity values of the associated fluorescence image to generate a set of representative intensity values, selecting a subset of the set of representative intensity values corresponding to the set of fluorescence images based on a predetermined criterion that is used to filter out one or more of the representative intensity values in the set of representative intensity values;

averaging the selected subset of representative intensity values to calculate an averaged intensity value; and calculating the patient-specific threshold based on the averaged intensity value and an adjustment factor associated with the pixel comparator.

18. The at least one non-transitory computer-readable storage medium of claim 17, wherein the fluorescence images are surgical site fluorescence images of a surgical site of the patient.

19. The at least one non-transitory computer-readable storage medium of claim 18, the method further comprising:
receiving a new surgical site fluorescence image;
identifying one or more groups of abnormal cells in the new surgical site fluorescence image based on the calculated patient-specific threshold; and
indicating, via a display, one or more locations of at least one of the one or more groups of identified abnormal cells.

20. The at least one non-transitory computer-readable storage medium of claim 15, wherein the pixel comparator is selected from the group consisting of:
- a maximums comparator that calculates the one or more representative intensity values for each fluorescence image in the set of fluorescence images by calculating a maximum pixel intensity value of each fluorescence image;
- a minimums comparator that calculates the one or more representative intensity values for each fluorescence image in the set of fluorescence images by calculating a minimum pixel intensity value of each fluorescence image;
- a means comparator that calculates the one or more representative intensity values for each fluorescence image in the set of fluorescence images by calculating a mean of pixel intensity values of each fluorescence image;
- a twenty-fifth percentile comparator that calculates the one or more representative intensity values for each fluorescence image in the set of fluorescence images by calculating a 25% percentile of pixel intensity values of each fluorescence image; and
- a medians comparator that calculates the one or more representative intensity values for each fluorescence image in the set of fluorescence images by calculating a median pixel intensity value for each fluorescence image.

21. The at least one non-transitory computer-readable storage medium of claim 17, the method further comprising selecting the pixel comparator from a plurality of pixel comparators, comprising:
- running the plurality of pixel comparators on a training set of images to calculate a set of results values for each of the pixel comparators in the plurality of pixel comparators;
- analyzing the set of results values for each pixel comparator in the plurality of pixel comparators; and
- selecting the pixel comparator from the plurality of pixel comparators based on the analysis.

22. The at least one non-transitory computer-readable storage medium of claim 17, wherein each fluorescence image in the set of fluorescence images is an image of healthy tissue.

23. The at least one non-transitory computer-readable storage medium of claim 17, wherein the adjustment factor is a multiplier.

24. The at least one non-transitory computer-readable storage medium of claim 23, wherein the multiplier ranges from 1 to 25.

* * * * *

UNITED STATES PATENT AND TRADEMARK OFFICE
CERTIFICATE OF CORRECTION

PATENT NO. : 11,793,594 B2
APPLICATION NO. : 16/708486
DATED : October 24, 2023
INVENTOR(S) : David B. Strasfeld et al.

Page 1 of 1

It is certified that error appears in the above-identified patent and that said Letters Patent is hereby corrected as shown below:

In the Claims

At Column 21, Claim 20, Line 2, please replace "claim 15" with -- claim 17 --

Signed and Sealed this
Twenty-eighth Day of November, 2023

Katherine Kelly Vidal
*Director of the United States Patent and Trademark Office*